United States Patent [19]

Lynn

[11] Patent Number: 4,838,855
[45] Date of Patent: Jun. 13, 1989

[54] BLOOD ASPIRATION ASSEMBLY AND METHOD

[76] Inventor: Lawrence A. Lynn, 4877 Dublin Falls, Columbus, Ohio 43220

[21] Appl. No.: 80,406

[22] Filed: Jul. 31, 1987

[51] Int. Cl.⁴ ............................................. A61M 31/00
[52] U.S. Cl. ..................................... 604/49; 128/764; 128/765; 128/766; 604/4; 604/183; 604/208; 604/248
[58] Field of Search ................ 128/760, 762, 764–766, 128/768, 771; 604/4, 8, 9, 48–50, 80–86, 118, 121, 124, 125, 131–135, 93, 181, 183, 184, 186, 187, 201, 205, 208, 236, 240, 244, 246, 248, 256, 280, 283, 284, 218, 220, 221, 222, 228, 27–29, 32, 35, 38

[56] References Cited

U.S. PATENT DOCUMENTS

| | | | |
|---|---|---|---|
| 2,357,238 | 8/1944 | Trimble | 604/4 |
| 2,847,996 | 8/1958 | Cohen et al. | 604/240 |
| 3,344,785 | 10/1967 | Hamilton | 604/4 |
| 4,013,064 | 3/1977 | Patel et al. | 604/86 |
| 4,051,852 | 10/1977 | Villari | 604/183 |
| 4,214,779 | 7/1980 | Losell | 604/86 |
| 4,219,021 | 8/1980 | Fink | 604/248 |
| 4,335,717 | 6/1982 | Bujan et al. | 604/83 |
| 4,364,383 | 12/1982 | Vcelka | 604/48 |
| 4,634,427 | 1/1987 | Hannula et al. | 604/93 |
| 4,763,648 | 8/1988 | Wyatt | 128/762 |
| 4,796,644 | 1/1989 | Polaschegg | 128/760 |

FOREIGN PATENT DOCUMENTS

0208975  1/1987  European Pat. Off. ............ 604/187

OTHER PUBLICATIONS

Brochure, Travenol Laboratories, Dialysis Products, 1984.
Article, Knox, Implantable Vascular Access Devices, pp. 70–73.
Article, Winters, Implantable Vascular Access Devices, Nov./Dec. 1984, pp. 25–30.
Article, Cannon, Arrington-Mitchell, & Fabian, Prospective Randomized Evaluation of Two Methods of Drawing Coagulation Studies from Heparinized Arterial Lines, Jul. 1985, pp. 392–395.
Article, Smoller, Kruskall, Phlebotomy for Diagnostic Laboratory Tests in Adults, May 8, 1986, pp. 1233–1235.

(List continued on next page.)

*Primary Examiner*—C. Fred Rosenbaum
*Assistant Examiner*—Mario Costantino
*Attorney, Agent, or Firm*—Rogers, Howell, Moore & Haferkamp

[57] ABSTRACT

A blood aspiration assembly and method has proximal, intermediate and distal tubing, a reservoir having an adjustable volume and an aspirator receiver. A two-way valve can connect the reservoir to the intermediate tube and block flow to the proximal tubing, or can connect the intermediate and proximal tubing while blocking flow to the reservoir. The reservoir can be locked into selected withdrawal and discharge positions. The intermediate tube is connected with the aspirator receiver. The receiver is connected with the distal tubing. The receiver has a housing comprising a rigid casing and a resilient plug. The valve and reservoir can be operated to withdraw resident fluid from the assembly flow channels distal thereto into the reservoir, and draw blood from the patient into the intermediate tube to remove resident fluid from the aspiration chamber. A needle from a separate syringe is inserted through the plug into the aspirator chamber and a blood sample withdrawn. The reservoir has a predetermined potential maximum fluid volume equal to that volume which, when withdrawn into the reservoir from the intermediate tube, results in the replacement of essentially all resident fluid in the aspiration chamber and that portion of the apparatus distal to the aspiration chamber by essentially undiluted blood. The reservoir volume is less than the total internal volume of the apparatus distal to the reservoir whereby withdrawal of fluid into the reservoir does not cause blood to flow into the reservoir. The intermediate tube can have an enlarged section of be spiralled.

59 Claims, 2 Drawing Sheets

OTHER PUBLICATIONS

Article, Burnum, Medical Vampires, May 8, 1986, pp. 1250–1251.

Article, Walrath, Stopcock: Bacterial Contamination in Invasive Monitoring Systems, Jan./Feb. 1979, pp. 100–104.

Article, MacArthur et al., Stopcock Contamination in an ICU, Jan. 1975, pp. 96–97.

Article, Bourke, Errors in Intraoperative Hematocrit Determination, Sep. 1976, pp. 357–359.

Article, Dennis et al., Effect of Sample Dilutions on Arterial Blood Gas Determinations, Dec. 1985, pp. 1067–1068.

BLOOD ASPIRATION ASSEMBLY AND METHOD

BACKGROUND AND SUMMARY OF THE INVENTION

This invention relates to human blood aspiration assemblies and methods of their use. It is necessary and indeed critical to frequently draw blood from patients having a broad variety of illnesses. Cumulative and repetitive blood sampling must be conducted in a number of instances. Such blood samples are often drawn through tubing systems that are connected to indwelling catheters to avoid the pain, inconvenience and potential complications of frequent penetration of the patient's skin.

These tubing systems are often maintained in near-constant direct fluid communication with the vasculature through the catheter, and are used for monitoring pressures within the vasculature, for fluid administration, or simply for maintaining a channel for easy access to the vascular system.

These tubing systems generally contain an electrolyte or dextrose solution when in fluid connection with the vasculature. The reflux of blood into such tubing systems is prevented by maintaining fluid pressure within such tubing equal to, or higher than, that in the vessel in which the catheter dwells. This pressure avoids thrombotic occlusion of the tubing system or catheter while allowing the system to remain patent, or unobstructed despite near constant fluid communication with the vascular system.

In the prior art, such an above-described system can have a proximal tubing segment portion which is closest to the high pressure source, a distal tubing segment which is closer to the catheter, and a channel which opens to the atmosphere (atmospheric channel). This channel is usually capped. A three-way stopcock is connected to the channel and is in line with the tubing. Normally the stopcock connects the proximal tubing to the distal tubing, with the atmospheric channel closed.

When a blood sample is desired, the cap covering the atmospheric channel is removed. A separate syringe is moved by the hand and its neck connected to the atmospheric channel. The stopcock is then turned to open the distal tubing to the syrringe. This places the vascular system in direct fluid communication with the syringe. Fluid can then be aspirated from the tubing and the vascular system into the syringe. Upon aspiration, the initial liquid entering the syringe is the resident fluid in the distal tubing segment.

After this, blood, diluted with such resident fluid, will enter the syringe. Finally, after all the resident fluid has been aspirated into the syringe, undiluted blood will enter the syringe and will entirely fill the distal tubing. The stopcock is then closed to the atmospheric channel, and the first syringe is detached from the stopcock. The first syringe is in many uses discarded. With premature infants or small babies, the diluted blood in the first syringe may be reinjected after the blood sample for testing is obtained. But there is a risk of clot formation, thrombosis or infection when this attempt to save blood is made.

A second syringe then must be attached to the atmospheric channel and the stopcock is reopened to the second syringe to thereby place the syringe in fluid communication with the distal tubing that is filled with undiluted blood.

Undiluted blood is then aspirated into the second syringe from the distal tubing and the vasculature in the amount desired for analysis. When sufficient blood is obtained, the stopcock is closed to the second syringe. The second syringe is removed. At this point in some cases, to save blood, the diluted blood is reinjected from the first syringe back into the stopcock with the aforesaid hazards of thrombosis, clotting and infection. The stopcock is thence commonly closed to the distal tubing and opened to produce liquid communication between the proximal tubing and the atmospheric channel.

Following this, the pressure in the more proximal tubing is increased to allow fluid to escape from the proximal tubing out the atmospheric channel to clear residual blood from this channel. Next, the cap is replaced over the atmospheric channel. The stopcock is then closed to the atmospheric channel and opened to the distal tubing segment to reestablish the original fluid communication between the proximal and distal tubing. Following this, the pressure is again increased in the proximal tubing so that fluid will enter the distal tubing from the proximal tubing, thereby forcing the fluid within the distal tubing back into the vascular system through the catheter. As a result, the tubing system again becomes entirely filled with electrolyte or dextrose solution.

Several problems exist in the prior art. First, the procedure often requires the initial sample of blood (which is obtained to clear the resident fluid from the tubing) to be discarded, since it is diluted by the withdrawal procedure. This results in a loss of blood from the patient which is cumulative over many sample aspirations. Eventually, this can produce anemia and could necessitate a blood transfusion to replace such cumulative blood losses. (See "Phlebotomy For Diagnostic Laboratory Tests In Adults, Pattern Of Use and Effect On Transfusion Requirements", *New England Journal Of Medicine*, Vo.. 31, p.1233, 1986; and "Medical Vampires" (Editorial), *New England Journal Of Medicine*, Vol. 31, p. 1250, 1986).

Patients who require many blood samples to be taken during protracted illnesses or after severe trauma may require transfusions which would not otherwise be necessary, and may therefore be subject to the increased risk of blood transfusion related infectious diseases such as hepatitis and A.I.D.S., for example.

Moreover, the stopcock in conventional systems must frequently be open to a channel which is intermittently exposed to the atmosphere. Hence, there is a significant risk of microorganisms contaminating the stopcock and thereby entering the vascular system producing infections which may be extremely serious and even fatal. (See "Stopcock: Bacterial Contamination and Invasive Monitoring Systems", *Heart and Lung*, Vol. 8, p. 100, 1979; and "Stopcock contamination In An ICU", *American Journal of Nursing*, Vol. 75, p. 96, 1975).

An additional problem is the potential for dilutional error introduced into the blood samples obtained. This results when hospital personnel fail to remove enough blood to adequately clear the resident fluid from the indwelling catheter and its connected tubing. This has been reported in the medical literature to cause error in both measured blood gas values and hematocrit concentrations. Such erroneous hematocrit values have been noted as a potential source of unnecessary blood transfusions in surgical patients. It has been noted that the first syringe must withdraw a volume of intravenous solution and blood that is six times the volume of the tubing distal to the stopcock. (See "Errors In Intraoperative Hematocrit Determination", *Anesthesiology*, Vol. 45, p. 357, 1976; and "Effect of Sample Dilutions on Arterial Blood Gas Determinations", *Critical Care Medicine*, Vol. 13, p. 1067, 1985).

Furthermore, many present conduit systems provide internal diameters which vary abruptly over the length of the conduit. The abrupt change in diameters results in areas where fluid flow is not streamlined, and where pockets of fluid can gather while the main fluid flow goes onward. Accordingly, when blood is drawn into the system from the catheter to displace the resident fluid, pockets of residual resident fluid may remain withing the conduit channel. This can dilute any aspirated blood samples later drawn.

Another shortcoming is that the present method of obtaining undiluted blood samples from fluid-filled tubing connected with the vascular system is cumbersome and inconvenient.

SUMMARY OF INVENTION

The present invention has features which improve over the art. The present invention allows aspiration of undiluted blood samples from tubing connected to arterial catheters without opening the tubing system to the atmosphere. With the present invention, there is no need to discard an initial blood sample. Hence, this invention eliminates the loss of blood samples through discard and reduces the potential for the introduction of microorganisms into the vasculature.

The features of the invention additionally reduce the exposure of hospital personnel to blood products, and hence reduces exposure of such personnel to contraction of diseases carried by blood products. With use of the present invention, there will be a reduction in the number of transfusions, especially in neonates and patients with protracted critical illnesses.

The invention may significantly reduce the incidence of nosocomial bacteremia and the associated morbidity and mortality caused by the introduction of microorganisms into tubing through conventional stopcocks. Moreover, the present invention simplifies the procedure. The invention reduces the potential for measurement error introduced by the dilution of the blood samples obtained.

An embodiment of the invention comprises proximal, intermediate and distal tubing sections. The proximal section can be in fluid flow connection with a source of higher fluid pressure. Such source can be a liquidfilled container of intravenous fluid such as dextrose or electrolyte, which is elevated or surrounded by a source of increased pressure, for example, a pressure bag. The proximal tubing section extends to a two-way valve. The two-way valve is further connected to the intermediate tubing section. The intermediate tubing is connected to an aspirator receiver. The aspirator receiver is in turn connected to the distal tubing. The distal tube connects to an indwelling catheter.

In one position, the valve connects the intermediate tubing with a reservoir. In the other position, the valve connects the intermediate tubing with the proximal tubing and hence with the aspirator receiver and the distal tubing.

A clamp or valve can be placed with the intermediate tubing to either block or permit liquid flow therethrough.

The aspirator receiver can comprise a housing in liquid communication with the intermediate and distal tubes. The housing has a portion comprising a resilient material, such as silicone. In an embodiment, part of the housing can be of rigid material which comprises a casing, and the resilient material can fit within a bore of the casing. The housing has a chamber in liquid flow communication with the distal and proximal tubes. The resilient material allows a needle to perforate it so that the needle enters the aspiration chamber. The resilient material automatically seals the perforation produced by the needle when the needle is withdrawn therefrom.

The casing bore can be frustum-shaped. The resilient material can be a plug of conforming shape. In an embodiment, the plug can be of slightly greater diameter than the diameter of the frustum bore so that the plug must be slightly compressed to completely fill the bore when inserted therein. Alternatively, the resilient portion and the casing can be molded together.

The insertion of a needle into the plug will be accommodated by elastic compression of the plug material against the needle. The chamber preferably comprises a cylindrical bore which abuts the plug apex. The plug apex curves to correspond to the curve of the chamber bore to allow smooth liquid flow and prevent trapping of blood or dextrose thereabout.

The reservoir has means for changing pressure within the reservoir, such as a piston which can be locked into both the fully extended intake or discharge positions. When the two-way valve connects the reservoir to the intermediate tube, liquid enters the reservoir from the intermediate tube when the reservoir pressure is below the intermediate tube pressure. Liquid is discharged into the intermediate tubing when the reservoir pressure is greater than the intermediate tube pressure. The intermediate tube can have an enlarged section, or a spiralled section. In either case, the intermediate tube is designed to accommodate substantial volume as will be described below with the linear distance from end to end of the intermediate tube shortened to facilitate handling and operation.

The reservoir has an internal liquid volume potential equal to X. The volume X is also equal to a volume of blood which, when withdrawn from the vasculature through the catheter, through the distal tubing, through the aspirator chamber, and a portion of the intermediate tubing, causes displacement of substantially all the resident fluid from the catheter, the distal tubing, aspiration chamber, and a portion of the intermediate tubing. When the reservoir is filled with volume X of liquid from the intermediate tube, the blood enters the catheter, and the catheter, the distal tubing, and the aspiration chamber, and a portion of the intermediate tubing are thus filled with essentially undiluted blood. Closure of the clamp or valve is preferably on the intermediate tubing at a point so that after the reservoir has been filled with volume X of aspirated liquid from the distal portion of the assembly, the clamp or valve can be closed to isolate a segment of the apparatus distal thereto which contains essentially undiluted blood. Alternatively, the reservoir may be locked in the filled position so that substantial fluid flow cannot occur from the intermediate tubing and the aspiration chamber when the above designated clamp is absent. The predesignated volume X relationship, therefore, provides for consistent and predictable dilution free blood aspiration from the aspirator receiver chamber as will be described below.

When the reservoir is filled and a volume X of fluid has entered the reservoir and a volume X of blood has entered the catheter and apparatus through the distal tip of the catheter, the column of fluid within the assembly comprises three basic segments which progressively merge together: a distal segment composed of substantially undiluted blood, an intermediate segment of blood mixed with resident fluid, and a proximal segment of resident fluid which contains essentially no blood. The sum of the internal potential fluid volumes of the catheter, the distal tubing segment, the aspirator receiver chamber, and the intermediate tubing is equal to a volume of Y. The volume Y is greater than the sum of the fluid volumes of the distal segment of essentially undiluted blood and the intermediate segment of blood-resident fluid admixture formed by the above described withdrawal maneuver. Therefore, a proximal portion of the intermediate tubing will contain resident fluid with essentially no blood after the volume X of blood has entered through the catheter into the assembly in response to the withdrawal of the volume X of resident fluid into the reservoir. The volume Y can be considerably larger than the volume X to accommodate variability in the volume of resident fluid which directly mixes with the blood. Thus, blood does not enter the reservoir during such withdrawal. Therefore, the predesignated volume Y relationship provides for prevention of the potential for blood clot formation within the reservoir by preventing blood from entering the reservoir during reservoir filling.

The invention is operated by first opening the two-way valve to connect the reservoir and the intermediate tube. The intermediate tube clamp or valve is open. The reservoir pressure is then reduced to be substantially less than the liquid pressure in the intermediate tube (if that pressure is already not substantially less). A volume of fluid equal to X then enters the reservoir from the intermediate tube. The reservoir then may be locked to maintain the volume X dimensions. A volume of blood equal to X will enter the catheter, distal tube, aspiration chamber, and part of the intermediate tube, as the resident fluid in those parts is displaced proximally through the apparatus, down the pressure gradient generated by the lower reservoir pressure. The intermediate tube clamp or valve is then closed to isolate the blood in the blood aspiration chamber and the part of the apparatus distal thereto, from the blood and liquid proximal to the clamp.

The blood now in the aspiration chamber, the distal tube, and the catheter is virtually undiluted blood. This is because the volume X is predetermined by design to be a volume which virtually completely displaces all resident liquid in juxtaposition with and distal to the aspiration point of the chamber (and distal to the clamp in the intermediate tube if provided) when said Volume X is withdrawn into the reservoir as described and replaced by blood entering through an indwelling catheter. A needle connected to a syringe or vacuum-filled container is then inserted through the resilient part of the aspirator receiver until the needle tip enters the blood filled chamber.

Blood is then aspirated into the syringe or container from the chamber with additional blood replacing the aspirated blood through the indwelling catheter. Either the locking of the reservoir fully in the withdrawn position (when the two-way valve connects the reservoir into the intermediate tube) or the closing of the intermediate tube clamp can prevent substantial flow of fluid from the intermediate tube into the aspirator receiver chamber. Both may be provided in the preferred embodiment to reduce the chance of procedural error during operation for the apparatus.

Once a satisfactory sample has been obtained, the syringe needle is withdrawn from the resilient section. The resilient section automatically seals the perforation produced by the needle. The clamp is then opened and the reservoir pressure raised so that the volume X of fluid will re-enter the intermediate tube from the reservoir. This produces a pressure gradient which drives much of the blood which previously entered the apparatus back into the vascular system. The two-way valve is then closed to the reservoir and positioned to place the intermediate and proximal tubes in liquid communication. The pressure in the proximal tube can then be increased if desired, to displace any residual blood from the apparatus into the vasculature.

It is therefore an object of the present invention to provide a method and apparatus of blood aspiration through indwelling catheter which does not require an intial diluted sample of blood to be collected and wasted (or exposed to a high risk of coagulation or contamination) before the undiluted specimen for analysis is collected.

It is further an object of the invention to provide a method and apparatus of blood aspiration through an indwelling catheter which does not require any channel in fluid connection with the vascular system to be exposed to the atmosphere.

Moreover, an object of the invention is to provide a method and apparatus of blood aspiration which reduces the exposure of hospital personnel to blood products and simplifies the blood aspiration process.

It is yet another object of the invention to provide a method and apparatus of blood aspiration which predictably reduces the risk of measurement error which may be introduced by the dilution of blood samples by fluid from within indwelling catheters or connected tubing.

An additional object of the invention is to provide a channel throughout which flow is substantially unobstructed and hence efficient in displacing resident liquid in the distal channel by blood entering through the catheter. This minimizes the potential for dilution of blood samples by residual pockets of resident liquid within the channel when blood is aspirated. This permits smaller blood samples to be taken with the maintenance of acceptable measurement accuracy.

DETAILED DESCRIPTION OF PREFERRED EMBODIMENT

Figures 1A, 2, 3, 4:
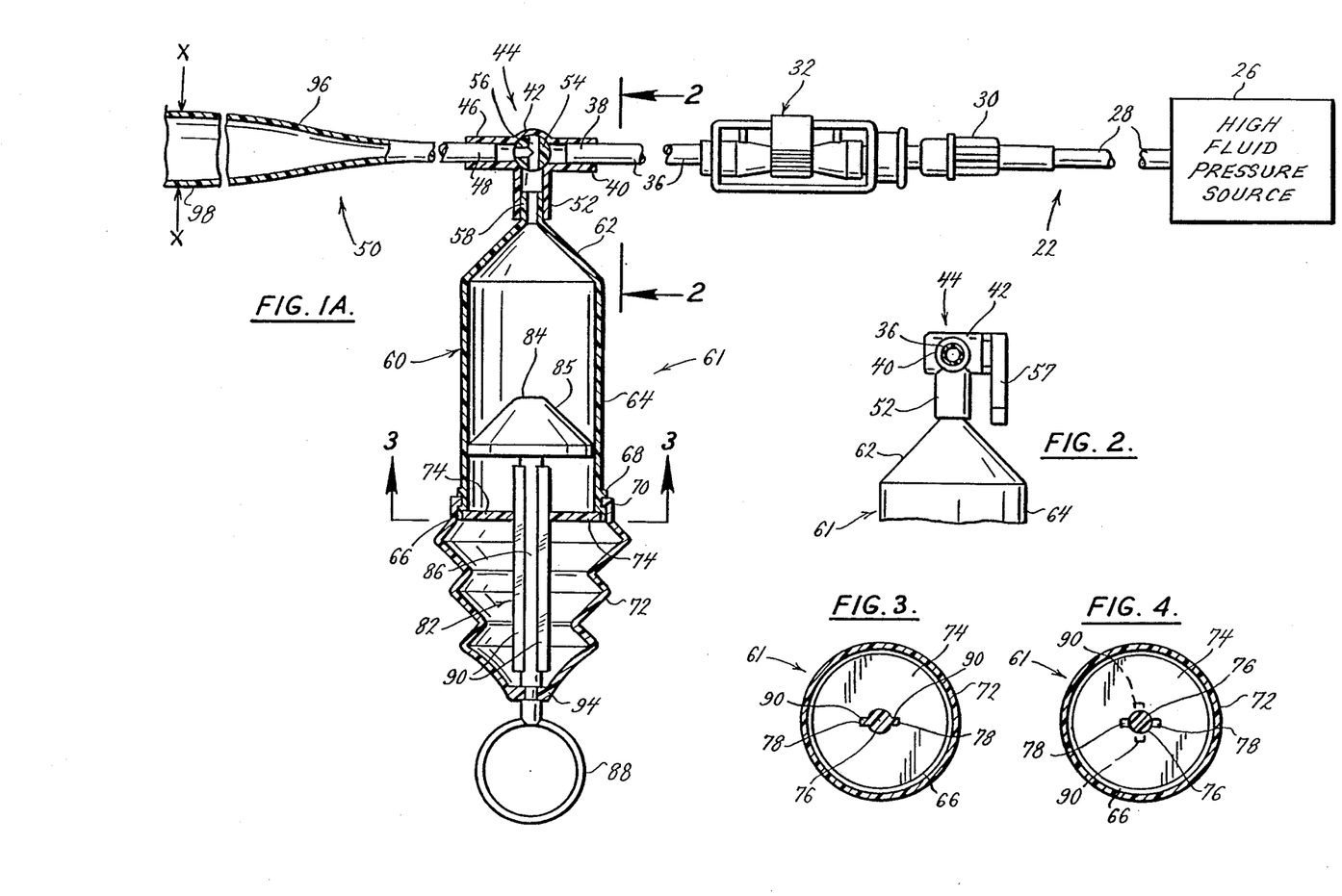
FIG. 1A shows the proximal part of the assembly, with some parts shown in section, and some parts broken, with a schematic for the high fluid pressure source.
FIG. 2 is a section taken on the line 2—2 of Fig. 1A.
FIG. 3 is a section of the reservoir, taken on the line 3—3 of FIG. 1A.
FIG. 4 is a section of the reservoir showing the piston rod turned to lock the rod and piston in the fully discharged position.
Figures 1B, 5, 6, 7, 8, 9, 10:
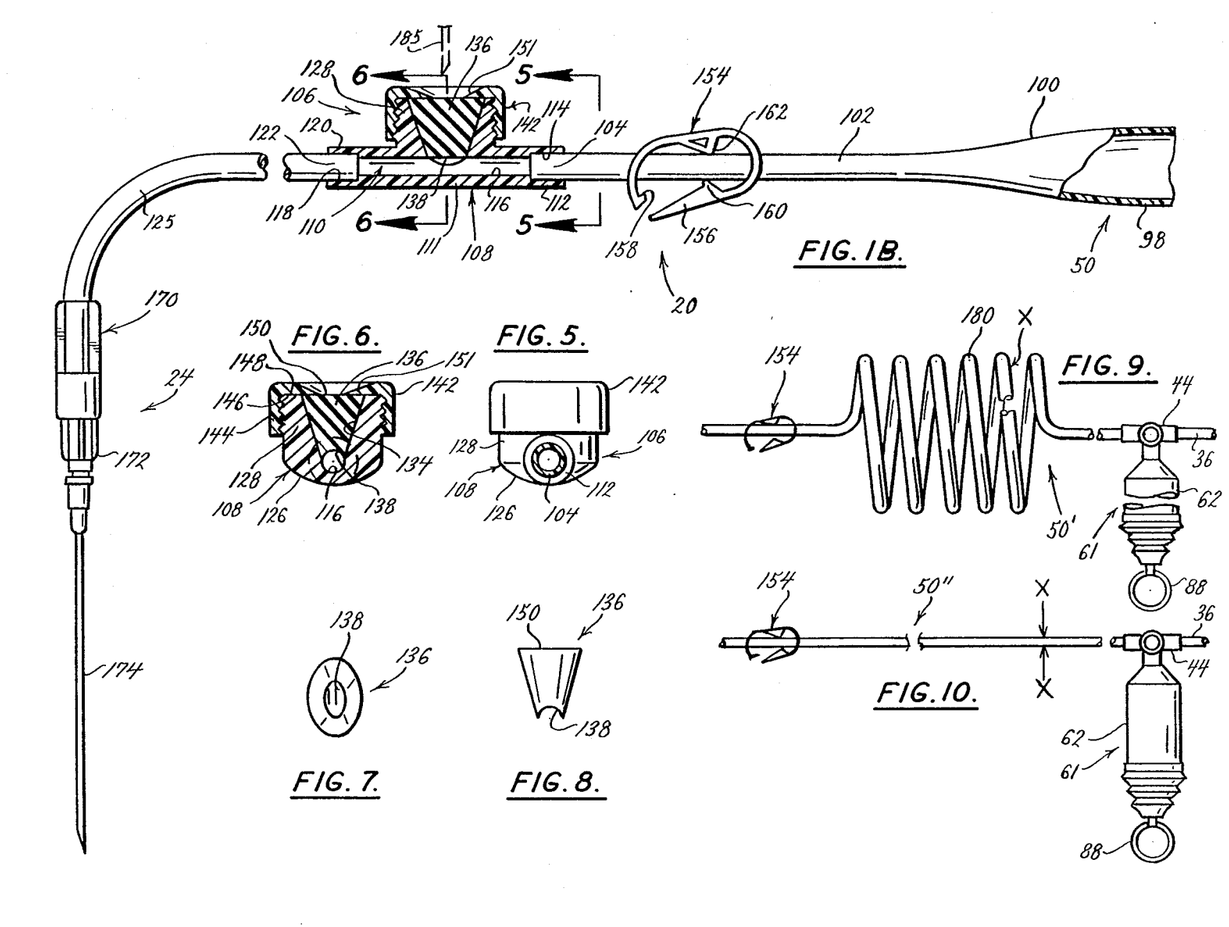
FIG. 1B shows the distal part of the assembly, with some parts shown in section and some parts broken.
FIG. 5 is a section of the assembly taken on the line 5—15 of FIG. 1B.
FIG. 6 is a section through the aspiration chamber taken on the line 6—6 of FIG. 1B.
FIG. 7 is a bottom plan view of the resilient portion of the aspiration chamber housing.
FIG. 8 is a side view of the resilient portion of the aspiration chamber housing.
FIG. 9 shows a modification wherein the intermediate tubing has a spiraled section.
FIG. 10 is a modification wherein the intermediate tubing is of the same diameter throughout and straight.

The blood aspiration assembly 20 has generally a proximal end 22 shown in FIG. 1A and a distal end shown generally as 24 in FIG. 1B. This description will work from the proximal end 22 toward the distal end 24. A high fluid pressure source shown schematically as 26 can comprise a fluid-filled container which is elevated, or which is surrounded by a source of increased pressure, for example, a pressure bag. Source 26 can have intravenous fluid therein. The pressure source 26 is in liquid flow connection with proximal flexible tubing section 28. Tubing 28 has its distal end connected by means known in the art to a coupling 30 for a trigger squeeze valve mechanism 32. The proximal tubing has another section 36 with its proximal end in liquid flow connection by known means to the distal end of trigger valve mechanism 32.

The distal end 38 of proximal tube section 36 is telescopically received within the port sleeve 40 of a housing 42 for a two-way valve 44. Valve housing 42 has a port sleeve 46 which telescopically receives the cylindrical end 48 of a flexible intermediate tube 50. Valve housing 42 further has a port sleeve 52 which is connected to a reservoir to be described.

The valve 44 has an interior body 54 having T-shaped flow channels 56, as known in the art, extending therethrough. Body 54 is rotatable by a handle 57. FIG. 1A shows valve body 54 positioned for liquid flow between ports 46 and 52, with flow from those ports to proximal port 40 being blocked. Handle 57 can rotate body 54 to connect ports 40 and 46 for liquid flow therebetween, and block flow from those ports to port 52. In the preferred embodiment, rotation of handle 57 is limited to ninety degrees so that port 40 cannot be connected to port 52. Rotation of handle 57 on 45° will block liquid flow between all three ports.

Port sleeve 52 telescopically receives and holds as by adhesive the cylindrical distal end 58 of a housing 60 of a reservoir 61. The housing 60 further comprises a frusto conical section 62 connected to distal end 58 and to a larger cylindrical section 64. The proximal end of section 64 has an outwardly jogging annular flange 66. Distal thereto is an annular rib 68 with an annular slot formed therebetween which receives the annular distal end 70 of an accordion pleated boot 72. Boot 72 can be of a flexible plastic with a plurality of pleated sections, as shown. At the proximal end of cylindrical section 64, a plastic disc 74 is mounted to telescopically fit within the slot formed interior of annular flange 66 and held as by adhesive. Disc 74 has a central cylindrical bore 76 having a pair of oppositely extending slots 78. Housing 60, disc 74 and valve housing 42 can be transparent plastic.

A plunger assembly 82 comprises a frustum-shaped piston 84 of plastic with slanted wall 85. Piston 84 is connected to a rod 86 which extends proximally into a ring handle 88. Part of rod 86 has a pair of oppositely extending linear lock flanges 90. Rod 86 and flanges 90 are sized to be snugly telescopically received through the conforming bore 76 and slots 78 in disc 74. Between ring 88 and flanges 90, rod 86 has an annular groove that receives and holds as by adhesive the annular proximal boot end 94.

The piston 84 is sized so that its outer extremeties are snugly and telescopically fitted against the interior of housing section 64. Piston 84 maintains a tight seal against section 64 to thus prevent liquid from passing from the distal to the proximal side of piston 84 during piston 84 compression.

Piston wall 85 conforms with the shape of reservoir housing wall 62 to be pressed snugly thereagainst when rod 86 is in the full discharge position. When piston 84 reaches this position, the proximal ends of lock flanges 90 extend just beyond the distal side of disc 74. To lock in this position handle 88 can then rotate rod 86 ninety degrees. Next, handle 88 is released. The proximal ends of flanges 90, having been rotated ninety degrees, press against the distal side of stop disc 74 to hold piston 84 locked in a discharge position (FIG. 4).

To move the piston 84 from this position to lock in the fully withdrawn position, the handle 88 can be rotated to align flanges 90 with slots 78. The handle 88 can be pulled proximally to move the distal ends of flanges 90 just beyond the proximal side of stop disc 74. Handle 88 is then rotated ninety degrees and released so that flanges 90 both extend perpendicular to the slots 78. The distal ends of flanges 90 abut the proximal side of stop disc 74 to lock rod 86 and piston 84 against distal movement.

Returning to intermediate tube 50, from its proximal end 48, tube 50 tapers at 96 into an enlarged section 98 which thence tapers at 100 (FIG. 1B) toward a smaller part 102. Part 102 extends into a distal tube end 104.

A blood aspirator receiver means 106 comprises a housing 108. Housing 108 includes a main liquid flow path or chamber 110. Housing 108 has a casing 111 which comprises a cylindrical sleeve 112 having an internal cylindrical bore 114. Bore 114 telescopically and snugly receives and holds tube end 104 as by adhesive. Bore 114 extends into and intersects a smaller central bore 116 which is part of chamber 110. Bore 116 extends distally to intersect with a larger bore 118 located within a distal sleeve 120 that is part of casing 111. Bore 118 telescopically receives and snugly holds as by adhesive the proximal end 122 of a flexible distal tube 125. As seen in FIGS. 5 and 6, the bottom of casing 111 located between sleeves 112 and 120 is rounded at 126 to provide additional strength.

Casing 111 has an externally threaded cylindrical extension 128 which is integral with sleeves 112 and 120. Extension 128 has an elliptical frustum-shaped bore 134. Bore 134 can be filled with a resilient material such as silicone rubber or the like to form a plug 136. Plug 136 is shown isolated in FIGS. 7 and 8. Plug 136 has a cylindrical arcuate bottom 138 of the same curvature as housing bore 116, as seen specifically in FIG. 6. As a result, liquid such as blood or dextrose solution, will flow smoothly through the portion of flow path or chamber 110 which is adjacent the juncture of plug bottom 138 with bore 116. This prevents any liquid such as dextrose solution or other initial resident fluid within housing 108 from accumulating within the flow path or chamber 110 when resident fluid is being withdrawn from aspirator receiver means 106.

The resilient plug 136 can be molded with the more rigid plastic casing 111 so that the plug 136 securely bonds to the bore 134. Alternatively, the plug 136 can be molded separately and installed in bore 134. In this case the truncated plug bottom 138 is of slightly greater diameter than the diameter of the apex of bore 134. The plug 136 must hence be slightly compressed to fill bore 134 when it is inserted therein.

The lateral expansion forces induced by accommodation of the additional volume of any needle inserted into plug 136 will be met by additional elastic compression of the resilient material, since the diameter of plug 136 cannot be increased due to the limitations of the surrounding bore 134. The resilient plug 136 can tightly seal the perforation produced by a needle through elastic reexpansion of the plug material after needle withdrawal.

The aspirator receiver means 106 further has a cap 142. Cap 142 has (FIG. 6) a depending internally threaded sleeve 144 to screw about extension 128. The inside surface 146 of cap top wall 148 screws flush against the flat top of extension 128 and the flat top 150 of plug 136. Cap wall 148 has a central funnel-shaped bore 151.

As seen in FIG. 5, the internal diameter of both tube ends 104 and 122 (not shown) is of the same internal diameter as housing bore 116 to likewise provide streamlined flow between tube ends 104 and 122 and bore 116. This prevents any buildup of dextrose solution or other resident fluid to avoid such buildup diluting any blood sample withdrawn from chamber 110, and also prevents buildup of blood when resident liquid reenters the housing 108 as will be described.

As seen in FIG. 1B, a plastic clamp 154 of the type commonly known in the art has openings at its proximal and distal ends to receive tube section 102. A lever arm 156 can be moved to have its end locked by catch 158 so that the tube 102 is clamped closed by the pincher points at 160 and 162.

Distal tube 125 extends distally to a female catheter connector fitting 170, as known in the art. The fitting 170 receives a catheter connector sleeve 172 which is connected to a catheter 174 as known in the art.

FIG. 9 shows a modification of the intermediate tube. The modified tube 50'has a spiralled or coiled tubing section 180 as opposed to the enlarged section 98 shown in FIGS. 1A and 1B. With either the FIG. 9 or FIGS. 1A and 1B version, the overall length of the intermediate tube is shorter than it would be if the intermediate tube had a uniform diameter such as that of the distal tube end 104, as pictured ad 50" in FIG. 10.

In operation, catheter 174 is indwelling and clamp 154 is open as shown in FIG. 1B. Piston 84 of reservoir 61 is in the maximum discharge position with its wall 85 abutting the interior of housing wall 62. The plunger rod 86 has its lock flanges 90 at a ninety degree angle with the slot 78 in stop disc 74, as shown in FIG. 4.

Valve 44 is positioned to connect port 40 to port 46. From this positioning, the intravenous fluid from the high fluid pressure source 26 has filled the tubing 28, the conduit in trigger 32, the tubing 36, the port sleeves 40 and 46, intermediate tubing 50, chamber 110, distal tubing 125, fitting 170, connector 172 and catheter 174.

With the valve 44 so positioned, the pressure within the blood vessel can be monitored, or fluid administered, depending on the function of the device, or devices, connected proximally to the tubing 28.

Valve 44 is then positioned to connect reservoir port 52 to distal port 46. In so doing, port 40 and hence source 26 are blocked from connection with ports 46 and 52.

Now the assembly 20 can be operated to withdraw blood from the patient for sampling. Plunger handle 88 rotates ninety degrees to align lock flanges 90 with disc slots 78. The handle is moved proximally until the distal ends of flanges 90 pass beyond disc 74. Handle 88 and rod 86 are rotated ninety degrees to lock rod 86 in this fully withdrawn position as aforesaid. In this position, the proximal flat end of piston 84 is adjacent the distal side of disc 74.

With the piston 84 so withdrawn, a volume X of resident intravenous fluid is drawn within the reservoir housing 60 from the port sleeves 52 and 46, and intermediate tube 50. As such withdrawal occurs, the resident fluid within catheter 174, connector 172 and fitting 170, distal tube 125 and chamber 110 moves into the intermediate tube 50.

Further as such withdrawal occurs, blood flows through catheter 174 into intermediate tube 50. The sum of the internal potential liquid volumes of catheter 174, connector 172 and fitting 170, distal tube 125, chamber 110, and intermediate tube 50, is equal to a volume of Y. The volume Y is greater than the sum of the liquid volumes of the distal segment of undiluted blood and the intermediate segment of blood-resident fluid admixture which are formed within assembly 20 by the flow of the volume X of blood into assembly 20 through catheter 174 as a result of withdrawing volume X of resident fluid into reservoir housing 60. This predesignated volume relationship allows for proximal end 48 of intermediate tube 50 to contain essentially only resident fluid after the volume X of resident fluid has been withdrawn into the reservoir housing 60 from the intermediate tube 50, so that blood does not enter the reservoir housing 60 during such withdrawal.

For purposes of illustration, the volume X which can be withdrawn into reservoir housing 60 is equal to the internal liquid volume of the flow channels distal to a point shown as X in FIGS. 1A, 9 and 10. After such withdrawal is complete, the flow channel within intermediate tube 50 contains a mixture of blood and resident fluid at the point shown as X. Distal to this point the blood-resident fluid mixture progressively merges with essentially undiluted blood such that only substantially undiluted blood is contained within the flow channels distal to the clamp pinch points 160 and 162. Proximal to the point marked X, the blood-resident fluid mixture progressively merges with resident fluid which contains substantially no blood such that only resident fluid is contained within the flow channel at proximal end 48 of intermediate tube 50. Therefore, with such withdrawal, blood replaces substantially all resident fluid within chamber 110 but does not enter reservoir housing 60.

Hence, after reservoir housing 60 is filled with fluid and clamp 154 closed, the blood aspiration chamber 110 and all tubing distal to the clamp pinch points 160 and 162 are filled with essentially undiluted blood which is virtually free of resident fluid and isolated from the proximal tubing system. The volume X is predetermined by design to allow adequate clearing of substantially all of the resident fluid from the blood aspiration chamber 110 and all tubing distal to the clamp pinch points 160 and 162 and volume Y is predetermined by design to prevent blood from entering the reservoir 61.

With the blood now in the aspiration chamber 110, aspiration of the blood for sampling can be conducted. Clamp 154 is moved to the closed position with the lever 156 held by catch 158 so that pinch points 160 and 162 press firmly against intermediate tube section 100 to block flow therein from one side of the points 160 and 162 to the other.

A needle 185 (FIG. 1B) of a typical needle syringe (not shown) or vacuum filled container (not shown) is moved through the funnel cap bore 151 to pass through plug 136 so that the needle point is inserted within the chamber 110. The syringe or vacuum filled container (not shown) aspirates as known in the art so that blood is aspirated from chamber 110 through needle 185 into the syringe or container (not shown). With this sample being taken, needle 185 is withdrawn from plug 136 and the sample of blood taken for proper analysis. Upon withdrawal of needle 185, the elastic material of plug 136 seals the needle perforation.

The withdrawn blood is replaced by additional blood from the patient flowing into catheter 174 toward chamber 110, since the clamp 154 has blocked off any liquid flow proximal of pinch points 160 and 162.

Following the taking of the blood sample and removal of needle 185, the clamp 154 can then be moved to the open position of FIG. 1B. Plunger handle 88 is rotated, moved to and locked in the fully discharged position with wall 85 abutting housing wall 62. This displaces the intravenous fluid from housing 60 back into the intermediate tube 50, chamber 110 and all tubing and connections distal thereto, thereby effectively clearing much of the residual blood from those flow paths. The two-way valve 44 is then rotated to connect ports 46 and 40 and block flow to and from reservoir port 52.

Any additional residual blood in the tubing and chamber 110 can be cleared by additional irrigation from the high fluid pressure source 26.

Cap 142 helps maintain plug 136 in the position shown, by counteracting any internal pressure in chamber 110 greater than atmospheric pressure, and resisting any tendency of the plug 136 to move with withdrawal of needle 185. The sloping surface of cap funnel bore 148 helps direct the needle 185 into the plug 136.

When the piston 84 is locked in the fully withdrawn position as aforesaid, such locking and holding of the reservoir 61 volume fixed will prevent flow of liquid from the second conduit toward the aspirator chamber 110 even when the clamp 154 is not employed. Hence, the locking of the piston 84 in such position is a means to inhibit flow of liquid in the second conduit toward the chamber 110 during aspiration through needle 185.

As known in the art, the trigger squeeze 32 can be operated to cause fluid flow from fluid source 26 into the assembly flow paths distal of trigger squeeze 32.

There are various changes and modifications which may be made to the invention as would be apparent to those skilled in the art. However, these changes or modifications are included in the teaching of the disclosure, and it is intended that the invention be limited only by the scope of the claims appended hereto.

What I claim is:

1. A blood aspiration assembly for use with a blood removal means inserted in a blood vessel of a patient and a separate aspirating means to remove blood from a patient, comprising:
   (a) means for providing a reservoir having a maximum displacement volume;
   (b) an aspirator receiver means having a chamber for permitting blood flow therein;
   (c) means for providing a first conduit for connecting the blood removal means to the aspirator receiver means so that the first conduit means is in liquid flow connection with the receiver chamber;
   (d) means for providing a second conduit connecting the aspirator receiver to the reservoir means so that the second conduit means can be in liquid flow connection with the receiver chamber; the second conduit means having an internal volume which is greater than the maximum displacement volume of the reservoir;
   (e) the aspirator receiver having a portion for receiving a part of the aspirating means to allow the aspirating means to be in blood flow connection with the aspirator receiver chamber so that blood drawn into the receiver chamber and into the first conduit means can be withdrawn from the aspirator receiver chamber and the first conduit means into the aspirating means.

2. The blood aspiration assembly of claim 1 further comprising means for making a volume of blood equal to the maximum displacement volume of the reservoir to flow from the blood vessel into the blood removal means, into the first conduit means, into the aspiration receiver chamber, and into a portion of the second conduit means, the second conduit means providing a capacitance function so that blood does not flow into the reservoir means.

3. The blood aspiration assembly of claim 1, further comprising the said receiver portion having means for sealing itself to block blood flow therethrough when the aspirating means is removed from the aspirator receiver.

4. The blood aspiration assembly of claim 1 further comprising means for inhibiting liquid flow through the second conduit so that when the aspirating means aspirates liquid from the receiver chamber, substantial liquid located within the second conduit does not flow into the aspiration receiver chamber.

5. The blood aspiration assembly of claim 4 wherein said means for inhibiting liquid flow through said second conduit comprises a liquid flow blocking means located between the reservoir and said aspirator receiver chamber.

6. The blood aspiration assembly of claim 5 wherein said means for inhibiting flow comprises a clamp located on the second conduit.

7. The blood aspiration assembly of claim 3 wherein the receiving portion of the receiver means comprises a resilient material.

8. The blood aspiration assembly of claim 7 wherein the resilient material comprises silicone.

9. The blood aspiration assembly of claim 7 wherein the receiver comprises a rigid section to which the receiving portion is associated, the rigid section extending to a side of the chamber opposite the resilient portion, the rigid section having a hardness and being sized to resist puncture by the aspirating means when normal forces are applied to the aspirating means against the rigid portion.

10. The blood aspiration assembly of claim 2 wherein the means for making blood flow includes the reservoir comprising a housing for containing liquid, the housing being in liquid flow connection with the second conduit means, means for creating suction in the housing to draw liquid from the second conduit into the reservoir housing, and to cause liquid flow from the blood removal means, the first conduit means and the receiver chamber toward the reservoir housing.

11. The blood aspiration assembly of claim 10 wherein the means for creating suction comprises the reservoir housing having a piston movably mounted therein so that piston movement in a selected direction creates suction to draw liquid from the second conduit into the reservoir housing.

12. The blood aspiration assembly of claim 11 further comprising the piston having a stroke for discharging liquid from the housing and for withdrawing liquid into the housing, and where means for inhibiting liquid flow through the second conduit comprises means for locking the piston in fixed position relative to the housing when the piston is in a fully withdrawn position.

13. The blood aspiration assembly of claim 12 further comprising means for locking the piston in fixed position relative to the housing when the piston is in a fully discharged position.

14. The blood aspiration assembly of claim 1 further comprising means for blocking liquid flow from the second conduit means to the reservoir.

15. The blood aspiration assembly of claim 14 wherein the means for blocking flow between the second conduit and the reservoir is a valve.

16. The blood aspiration assembly of claim 1 further comprising means for providing a third conduit, the third conduit having means for liquid flow connection to the second conduit.

17. The blood aspiration assembly of claim 16 wherein the means for liquid flow connection comprises a valve having a first position and a second position, which in the first position permits liquid flow from the third conduit means to the second conduit means and blocks liquid flow from the first and second conduit means to the reservoir, and in the second position blocks liquid flow from the third conduit means to the second conduit means but permits liquid flow from the second conduit to the reservoir.

18. The blood aspiration assembly of claim 9 wherein the receiver comprises a tubular portion, a rigid extension projecting generally radially from the tubular portion, the extension having means for mounting the resilient portion.

19. The blood aspiration assembly of claim 18 wherein the means for mounting comprises the extension having a bore to receive the resilient portion.

20. The blood aspiration assembly of claim 19 wherein the resilient portion is a plug shaped to fit within the bore of the extension.

21. The blood aspiration assembly of claim 19 wherein the resilient portion is a plug having a generally frustum shape, and the extension bore generally is frustum shaped.

22. The blood aspiration assembly of claim 9 wherein the receiver chamber is formed by the rigid section of the receiver means and by the resilient material portion of the receiver means, an interface between the rigid section and resilient material portion, the said interface being smooth so as to provide smooth flow of liquid in the chamber as liquid flows past the interface of the resilient material portion with the rigid section.

23. The blood aspiration assembly of claim 23 wherein in the preamble the blood removal means comprises a needle; and the body of the claim further comprising a cap, means for securing the cap to the extension, the cap having a hole for alignment with the resilient portion so that a needle can pass through the cap hole through the resilient portion and into the chamber.

24. The blood aspiration assembly of claim 22 wherein the chamber is of cylindrical shape.

25. A blood aspiration assembly for use with an insertion catheter to be inserted in a blood vessel of a patient and a separate aspirating means with a needle having a bore to remove blood from a patient, comprising:
    (a) means for providing a reservoir, the reservoir having means to vary the internal volume of the reservoir and a maximum displacement volume;
    (b) means for receiving the separate aspirating needle, the said receiving means having a chamber for permitting blood flow therethrough, the receiving means comprising a housing which includes a rigid casing and a resilient portion associated with the casing, the resilient portion being positioned with the casing so that the separate aspiration needle can penetrate the resilient portion to enter the chamber to be in liquid flow communication therewith;
    (c) means for providing a first conduit for connecting the catheter to the receiving means so that the first conduit means is in liquid flow connection with the receiver chamber;
    (d) means for providing a second conduit for passing liquid in either direction, the second conduit means connecting the receiver to the reservoir means so that the second conduit means can be placed in liquid flow connection with the receiving means chamber, the second conduit means having an internal volume which is greater than the maximum displacement volume of the reservoir;
    (e) means for providing a third conduit;
    (f) a valve connected between the reservoir and the second conduit means, the valve having means for being placed in a first position so that the reservoir means is in liquid flow connection with the second conduit, and the valve having means to be placed in a second position to place the third conduit means in liquid flow connection with the second conduit means;
    (g) the reservoir having means for creating a pressure differential to cause liquid to flow from the second conduit into the reservoir means when the valve connects the reservoir means to the second conduit for liquid flow therebetween; and
    (h) means for inhibiting liquid flow in the second conduit means so that when said means inhibits flow in the second conduit and when blood is aspirated from the receiver chamber through the needle into the separate aspirating means, additional blood flowing into the receiver chamber and into the first conduit comes from the patient and substantial blood does not flow from the second conduit into the aspirating means.

26. The blood aspiration assembly of claim 25 wherein the means for varying the volume of the reservoir means has a fully discharged and fully withdrawn position, and further comprising means for locking the means for varying the volume of the reservoir in the fully withdrawn position.

27. A method of aspirating blood from a human through the use of blood removal means connected to a first conduit, the first conduit being connected to an aspirator receiver having a chamber, the said chamber connected to a second conduit, the second conduit connected to a reservoir, the reservoir having a maximum displacement volume, the first conduit, the aspirator receiver chamber, and the second conduit being filled with intravenous fluid; and through use of a separate aspirating means having a needle, comprising the steps of:
 (a) causing a volume of intravenous fluid to flow through the second conduit into the reservoir which volume of fluid is less than the internal flow volume of the second conduit and which volume is equal to the maximum displacement volume of the reservoir, the said flow of intravenous fluid causing a volume of blood equal to the maximum displacement volume of the reservoir to enter the first conduit, the receiver chamber and a portion of the second conduit so that blood does not flow into the reservoir;
 (b) inhibiting flow of fluid toward the receiver chamber from the second conduit;
 (c) inserting the needle from the separate aspirating means into the receiver chamber and aspirating blood therefrom and withdrawing the needle from the receiver; and
 (d) substantially sealing the aspirator receiver about the entry point of the separate aspirating needle.

28. The method of claim 29 further comprising the step of discharging intravenous fluid from the reservoir into the second conduit so that intravenous fluid forces blood within the aspirator receiver chamber, the first conduit and the blood removal means back into the vessel of the patient.

29. An assembly for use with a blood removal means inserted in a blood vessel of a patient, for repetitive isolation of a volume of blood for testing or sampling, comprising:
 (a) means for providing an enclosed flow channel capable of being filled with liquid, the said flow channel having means for being in liquid flow connection with the blood removal means, and means for being in liquid flow connection with a liquid source having a pressure greater than the pressure within the said blood vessel;
 (b) the channel having a blood analysis section;
 (c) means for providing a reservoir, the reservoir means having a maximum displacement volume, the reservoir means further having means for withdrawing a volume of blood equal to said maximum displacement volume from the blood vessel into said channel;
 (d) means for retaining all of said displacement volume of blood entering the assembly within the flow channel when the withdrawing means withdraws a volume of blood equal to the maximum displacement volume of the reservoir means;
 (e) means for returning essentially all the said displacement volume of the blood in the flow channel back through the blood removal means into the patient's said blood vessel, the returning blood being moved in a direction within the said flow channel that is opposite the direction of blood entry into the flow channel.

30. The assembly of claim 29 wherein the reservoir has a variable volume, and the reservoir comprises a housing for containing liquid and having means for liquid connection to the analysis section of said channel, the reservoir having means for reducing the pressure within said reservoir below the pressure within the blood vessel, and having means for increasing said reservoir pressure above said blood vessel pressure.

31. The assembly of claim 30 wherein the means for retaining all of said displacement volume of blood comprises means for providing a flow channel capacitance segment, the said segment being intermediate the reservoir and the analysis section and wherein intravenous liquid can initially be received within the capacitance segment channel, the said segment having an internal volume which is greater than the maximum displacement volume of the reservoir.

32. The assembly of claim 31 further comprising means for blocking liquid flow between the reservoir and the higher pressure source.

33. The assembly of claim 32 wherein the means to block flow comprises a valve, the valve having means for alternately allowing liquid flow connection between the reservoir and the blood removal means while blocking flow from the higher pressure source, or between the higher pressure source and the blood removal means while blocking flow from the reservoir.

34. The assembly of claim 30 wherein the means for reducing reservoir pressure and means for increasing reservoir pressure comprises a piston movably mounted within the reservoir.

35. The assembly of claim 34 further comprising means for locking the piston relative to the housing in a fully withdrawn position to maintain a fixed internal liquid volume within the reservoir.

36. The assembly of claim 35 wherein the means for locking the piston comprises a rod having a longitudinal axis, the rod and the reservoir housing having means for interlocking to hold the piston in a fully withdrawn position.

37. The assembly of claim 36 wherein the means for locking comprises the reservoir housing having an opening to allow sliding movement of the longitudinal axis of the rod therethrough, and wherein the rod has a variance in its transverse width along part of its longitudinal axis so that when the rod is moved to a selected position relative to the housing opening, a portion of the rod having the variance can be moved to engage the reservoir housing to lock the rod to the housing.

38. The assembly of claim 36 further comprising a flexible sleeve connected to the reservoir housing and connected to the rod to provide a seal about the housing opening.

39. The assembly of claim 31 wherein at least part of the enclosed flow channel is intermediate the analysis section and the blood removal means, and wherein the capacitance segment has an internal diameter greater than the diameter of the said part of the flow channel between the blood removal means and the analysis section.

40. The assembly of claim 39 wherein the means for being in flow connection with the higher pressure source comprises a conduit which is in liquid flow connection with the capacitance segment, the said conduit having a smaller internal diameter than the internal diameter of the capacitance segment.

41. The assembly of claim 40 wherein the capacitance segment is connected to the conduit by a channel segment having a tapered portion of a general frustum shape.

42. The assembly of claim 31 wherein the capacitance segment comprises a coil segment.

43. The assembly of claim 32 further comprising means for permanently preventing liquid flow connection between the higher pressure source and the reservoir, said means having means for providing liquid flow connection between the high pressure source and the blood analysis section while preventing connection between the high pressure source and the reservoir.

44. The assembly of claim 29 wherein the blood analysis section has means to receive a means for blood aspiration for blood sampling.

45. An assembly for use with a blood removal means inserted in a blood vessel of a patient, for repetitive isolation of a volume of blood for testing or sampling, comprising:
   (a) means for providing an enclosed flow channel capable of being filled with liquid and for passing liquid in either direction, the said flow channel having means for being in liquid flow connection with the blood removal means, and means for being in liquid flow connection with a liquid source having a pressure greater than the pressure within the said blood vessel;
   (b) the channel having a blood analysis section, the said section having means for receiving a means for aspiration of blood for sampling;
   (c) means for providing a reservoir, the reservoir means having a maximum displacement volume, the reservoir means further having means for withdrawing a volume of blood equal to said maximum displacement volume from the blood vessel into said channel;
   (d) means for providing a flow channel capacitance segment, the said segment being intermediate the reservoir and the analysis segment, wherein intravenous liquid can initially be received within the capacitance segment channel, the said segment having an internal volume which is greater than the maximum displacement volume of the reservoir;
   (e) means for returning essentially all the said displacement volume of the blood in the flow channel back through the blood removal means into the patient's said blood vessel, the returning blood being moved in a direction within the said flow channel that is opposite the direction of blood entry into the flow channel.

46. In a blood aspiration assembly having a blood removal means with a set internal flow volume, the blood removal means being for insertion in a blood vessel of a patient, and a separate aspirating means for removing blood from a patient,
   (a) means for providing a reservoir having a displacement volume and means for indicating when a specific displacement volume has entered the reservoir;
   (b) means for providing an aspirator receiver having a chamber for permitting blood flow therein;
   (c) means for providing a first conduit for connecting the blood removal means to the aspirator receiver means so that the first conduit means is in liquid flow connection with the receiver chamber;
   (d) means for providing a second conduit for passing liquid in either direction, the second conduit means connecting the aspirator receiver means to the reservoir means so that the second conduit means can be in liquid flow connection with the receiver chamber;
   (e) the aspirator receiver means having a portion for receiving a part of the aspirating means to allow the aspirating means to be in blood flow connection with the aspirator receiver chamber so that blood drawn into the receiver chamber and into the first conduit means can be withdrawn from the aspirator receiver chamber and the first conduit means into the aspirating means;
   (f) means for making a predesignated volume of blood to flow from the blood vessel into the blood removal means, into the first conduit means, and into the aspiration receiver chamber, and into a portion of the second conduit means; the second conduit means providing a capacitance function so that blood does not flow into the reservoir means; the predesignated volume of blood being equal to the said specific displacement volume of the reservoir and which is equal at least to the internal flow volume of the blood removal means, the first conduit means and the aspirator receiver chamber; and
   (g) the predesignated volume of blood being less than the internal flow volume of the blood removal means, the first conduit means, the aspirator receiver chamber, and second conduit means.

47. The blood aspiration assembly of claim 46 wherein when the blood removal means, the first conduit means, the receiver chamber and the second conduit means initially have their internal flow volumes filled substantially with resident intravenous liquid, the means for making a predesignated volume of blood flow further making a sufficient amount of blood flow through the device to substantially replace the resident liquid in the blood removal means, the first conduit means and the receiver chamber with substantially undiluted blood.

48. The blood aspiration assembly of claim 47 further comprising means for inhibiting liquid flow through the second conduit so that when the aspirating means aspirates liquid from the receiver chamber, substantial liquid located within the second conduit does not flow into the aspiration receiver chamber.

49. The blood aspiration assembly of claim 48 wherein said means for inhibiting liquid flow through said second conduit comprises a liquid flow blocking means located between the reservoir and said aspirator receiver chamber.

50. The blood aspiration assembly of claim 49 wherein said means for inhibiting flow comprises a clamp located on the second conduit between said aspirator receiver means and said reservoir.

51. The blood aspiration assembly of claim 50 wherein the receiving portion of the receiver means comprises a resilient material.

52. The blood aspiration assembly of claim 51 wherein the blood aspiration means is a stainless steel needle, and wherein the receiver means comprises a rigid section to which the receiving portion is associated, the rigid section extending to a side of the chamber opposite the resilient portion, the rigid section having a hardness and being sized to resist puncture by the steel needle when normal forces are applied to the aspirating means against the rigid portion.

53. The blood aspiration assembly of claim 46 wherein the means for making blood flow includes the reservoir comprising a housing for containing liquid, the housing being in liquid flow connection with the second conduit means, means for creating suction in the housing to draw liquid from the second conduit into the reservoir housing, and to cause liquid flow from the blood removal means, the first conduit means and the receiver chamber toward the reservoir housing.

54. The blood aspiration assembly of claim 53 wherein the means for creating suction comprises the reservoir housing having a piston movably mounted therein so that piston movement in a selected direction creates suction to draw liquid from the second conduit into the reservoir housing.

55. The blood aspiration assembly of claim 54 further comprising the piston having a stroke for discharging liquid from the housing and for withdrawing liquid into the housing, and where the means for inhibiting liquid flow through the second conduit comprises means for locking the piston in fixed position relative to the housing when the piston is in a fully withdrawn position.

56. The blood aspiration assembly of claim 55 further comprising means for locking the piston in fixed position relative to the housing when the piston is in a fully discharged position.

57. The blood aspiration assembly of claim 46 further comprising means for blocking liquid flow from the second conduit means to the reservoir.

58. The blood aspiration assembly of claim 46 further comprising means for providing a third conduit, the third conduit having means for liquid flow connection to the second conduit, and wherein the means for liquid flow connection comprises a valve having a first position and a second position, which in the first position permits liquid flow from the third conduit means to the second conduit means and blocks liquid flow from the first and second conduit means to the reservoir, and in the second position blocks liquid flow from the third conduit means to the second conduit means but permits liquid flow from the second conduit to the reservoir.

59. The blood aspiration asseembly of claim 46 wherein the resilient portion comprises a plug shaped to fit with the aspirator receiver means, and wherein the receiver chamber is formed by the rigid part of the receiver means and by the resilient portion and wherein the inner face between the rigid part and the resilient portion is smooth so as to provide smooth flow of liquid in the chamber as liquid flows past the inner face of the resilient portion with the rigid part.

* * * * *